US011113808B2

(12) United States Patent
Kulkarni Wadhonkar et al.

(10) Patent No.: US 11,113,808 B2
(45) Date of Patent: Sep. 7, 2021

(54) SYSTEM AND METHOD FOR ASSESSING QUALITY OF PRODUCE

(71) Applicant: Walmart Apollo, LLC, Bentonville, AR (US)

(72) Inventors: Mangesh N. Kulkarni Wadhonkar, Hyderabad (IN); Parul Aggarwal, Samrala (IN); Anika Setia, Bangalore (IN); Akshay Jindal, Udaipur (IN); Rahul Kumar, Bangalore (IN); Amit Jhunjhunwala, Bangalore (IN); Artur A. Grochala, Dallas, TX (US)

(73) Assignee: Walmart Apollo, LLC, Bentonville, AR (US)

( * ) Notice: Subject to any disclaimer, the term of this patent is extended or adjusted under 35 U.S.C. 154(b) by 0 days.

(21) Appl. No.: 16/745,195

(22) Filed: Jan. 16, 2020

(65) Prior Publication Data

US 2020/0250802 A1    Aug. 6, 2020

Related U.S. Application Data

(60) Provisional application No. 62/826,102, filed on Mar. 29, 2019.

(30) Foreign Application Priority Data

Feb. 4, 2019   (IN) .............................. 201941004270

(51) Int. Cl.
*G01N 33/02*   (2006.01)
*G06T 7/00*   (2017.01)
(Continued)

(52) U.S. Cl.
CPC ........... *G06T 7/001* (2013.01); *G01N 33/025* (2013.01); *G06K 9/628* (2013.01);
(Continued)

(58) Field of Classification Search
CPC .. G06F 3/017; G06F 3/04842; G06F 3/04847; G06Q 30/0641; G06Q 20/12;
(Continued)

(56) References Cited

U.S. PATENT DOCUMENTS 5,152,401 A   10/1992   Affeldt, Jr.
5,589,209 A   12/1996   Mizrach
(Continued)

FOREIGN PATENT DOCUMENTS

CN   101603927   12/2009
CN   103487147 B   1/2014
(Continued)

OTHER PUBLICATIONS

Machine translation of JP-2001-062407-A, retrived Dec. 2, 2020, 14 pages. Retrieved: https://patents.google.com/patent/JP2001062407A/en?oq=JP+2001062407+A+ (Year: 2020).*
(Continued)

*Primary Examiner* — Matthew C Bella
*Assistant Examiner* — Dennis Rosario
(74) *Attorney, Agent, or Firm* — Fitch, Even, Tabin & Flannery LLP (57) ABSTRACT

In some embodiments, apparatuses and methods are provided herein useful to assess quality of produce at a facility. In some embodiments, there is provided a system for assessing quality of produce at a facility including a produce assessment station configured to provide a staging area to determine a quality classification of a target produce. By one approach, the produce assessment station includes a fixed surface; a rotatable base, a first arm comprising a microphone; a second arm comprising a tapping device; and a local control circuit. In one configuration, the local control circuit configured to rotate the rotatable base at a particular angle and at a particular time interval and receive audio data
(Continued)

from the microphone. By one approach, the system includes a plurality of sensors and a portable device configured to provide a signal to the local control circuit to initiate the quality classification of the target produce.

23 Claims, 5 Drawing Sheets

(51) Int. Cl.
 *G06K 9/62* (2006.01)
 *G06Q 10/06* (2012.01)
 *G10L 25/51* (2013.01)
(52) U.S. Cl.
 CPC ........ *G06Q 10/06395* (2013.01); *G10L 25/51* (2013.01); *G06T 2207/30128* (2013.01)
(58) Field of Classification Search
 CPC ......... G06Q 30/0631; G06Q 10/06395; H04N 21/4394; G06K 9/4671; G06K 2209/17; G06T 2207/30168; G06T 7/0002; G06T 2207/30128; G01N 33/025; A23V 2002/00
 See application file for complete search history.

(56) References Cited

U.S. PATENT DOCUMENTS

| | | | |
|---|---|---|---|
| 5,708,271 | A | 1/1998 | Ito |
| 5,822,068 | A | 10/1998 | Beaudry |
| 6,240,766 | B1 | 6/2001 | Cawley |
| 6,276,536 | B1 | 8/2001 | Terasaki |
| 6,363,366 | B1 | 3/2002 | Henty |
| 6,484,122 | B1 * | 11/2002 | Maetschke ........... G06K 9/6228 702/179 |
| 7,173,246 | B2 | 2/2007 | Benedetti |
| 7,930,259 | B2 | 4/2011 | Hashimoto |
| 8,072,605 | B2 | 12/2011 | Costa |
| 9,551,616 | B2 * | 1/2017 | McQuilkin ............ A22B 5/007 |
| 2004/0149916 | A1 | 8/2004 | Benedetti |
| 2017/0091748 | A1 | 3/2017 | Clark |

FOREIGN PATENT DOCUMENTS

| | | |
|---|---|---|
| CN | 103592367 | 2/2014 |
| CN | 107079665 | 8/2017 |
| EP | 1924839 | 5/2008 |
| JP | 200141941 | 2/2001 |
| JP | 2001062407 A * | 3/2001 |

OTHER PUBLICATIONS

Bianchi et al., External maturity indicators, carotenoid and sugar compositions . . . in 'Cuoredolce®' and 'Rugby' mini-watermelon . . . in relation of ripening degree, Feb. 2018 [retri Dec. 3, 2020], Postharvest Biology and Technology, vol. 136.,11 pages. https://doi.org/10.1016/j.postharvbio.2017.09.009 (Year: 2018).*
Tamburini et al., Quantification of Lycopene, β-Carotene, and Total Soluble Solids in Intact Red-Flesh Watermelon . . . Using On-Line Near-Infrared Spectroscopy, Apr. 11, 2017 [retr Dec. 3, 2020], Sensors 2017, vol. 17(iss 4), artel 746,12 pages. Retrived: https://www.mdpi.com/1424-8220/17/4/746 (Year: 2017).*
Hallur et al., Design and development of a portable instrument for the detection of artificial ripening of banana fruit, Nov. 21-22, 2014 [retrieved Dec. 3, 2020], International Conference on Circuits, Comm, Cntrl and Compting, pp. 139-140. Retrieved: https://ieeexplore.ieee.org/abstract/document/7057776 (Year: 2014).*
Abbaszadeh, R.; "Prediction of Watermelon Consumer Acceptability Based on Vibration Response Spectrum"; International Journal of Biological, Biomolecular, Agricultural, Food and Biotechnical Engineering; vol. 5, No. 6, 2011; pp. 364-368.
Bhattacharjee J.; "Some Key Machine Learning Definitions" Ninelaps; Oct. 27, 2017; pp. 1-4.
Gao, H. "A Review of Non-destructive Detection for Fruit Quality"; https://hal.inria.fr/hal-01061726; Sep. 8, 2014; pp. 1-10.
Karwa, A.; "Android Based Application for Fruity Quality Analysis"; International Journal of Innovation Research in Science, Engineering and Technology; vol. 5, Issue 12, Dec. 2016; pp. 20480-20487.
Koc, A.; "Determination of Watermelon Volume Using Ellipsoid Approximation and Image Processing"; Postharvest Biology and Technology; vol. 45, Issue 3, Sep. 2007; pp. 1-2.
Lakshmi, S.; "Non-destructive Quality Monitoring of Fresh Fruits and Vegetables"; Defence Life Science Journal; vol. 2, No. 2, Apr. 2017; pp. 103-110.
Librosa; "LibROSA"; https://librosa.github.io/librosa/; Available as early as Oct. 3, 2018; pp. 1-3.
Mizrach, A.; "Ultrasonic Technology for Quality Evaluation of Fresh Fruit and Vegetables in Pre-and Postharvest Processes"; Postharvest Biology and Technology; vol. 48, Issue 3, Jun. 2008; pp. 1-2.
P.S., S.; "Nondestructive Quality Evaluation for Fruits and Vegetables"; International Journal of Modern Trends in Engineering and Research; vol. 3, Issue 8, Aug. 2016; pp. 1-7.
Rajan, R.; "Non-destructive Classification of Watermelon Ripeness Using Acoustic Cues"; https://www.taylorfrancis.com/books/e/9781351124140/chapters/10.1201/9781351124140-116; Jan. 18-20, 2018; pp. 1-2.
Romadlon, F.; "Development of a Simple Instrument to Determine Watermelon Consumer Acceptance Based on its Amplitude"; Proceedings of 117th IASTEM International Conference; May 30-31, 2018; pp. 1-5.
Saldana, E.; "Review: Computer Vision Applied to the Inspection and Quality Control of Fruits and Vegetables"; Brazilian Journal of Food Technology; vol. 16, No. 4; Oct./Dec. 2013; pp. 1-19.
Sas; "Machine Learning: What it is and Why it Matters"; https://www.sas.com/en_us/insights/analytics/machine-learning.html; Jan. 19, 2019; pp. 1-12.
Simonyan K; "Very Deep Convolutional Networks for Large-Scale Image Recognition"; https://arxiv.org/pdf/1409.1556.pdf; pp. 1-14.
Slaughter, D.; "Nondestructive Quality Measurement of Horticultural Crops"; http://ucce.ucdavis.edu/files/datastore/234-2546.pdf; Jun. 16, 2013; pp. 1-14.
United States Department of Agriculture; "United States Standards for Grades of Watermelons"; https://www.ams.usda.gov/sites/default/files/media/Watermelon_Standard%5B1%5D.pdf; Mar. 23, 2006; pp. 1-11.
United States Department of Agriculture; "Watermelon Grades and Standards"; https://www.ams.usda.gov/grades-standards/watermelon-grades-and-standards; Jan. 17, 2019; pp. 1-3.
Weather-API; "A Python Wrapper for the Yahoo Weather API"; https://pypi.org/project/weather-api/; Dec. 28, 2018; pp. 1-4.
Wikipedia; "Artificial Neural Network"; https://en.wikipedia.org/wiki/Artificial_neural_network; Available as early as Oct. 3, 2018; pp. 1-43.
Wikipedia; "Convolutional Neural Network"; https://en.wikipedia.org/wiki/Convolutional_neural_network; Available as early as Oct. 3, 2018; pp. 1-24.
Zerbini, P.; "Emerging Technologies for Non-Destructive Quality Evaluation of Fruit"; http://www.insad.pl/files/journal_pdf/Suppl_2_2006/Suppl_2_full_1_2006.pdf; 2006; pp. 1-12.
PCT; App. No. PCT/US2020/015568; International Search Report and Written Opinion dated Apr. 16, 2020.

* cited by examiner

SYSTEM AND METHOD FOR ASSESSING QUALITY OF PRODUCE

CROSS-REFERENCE TO RELATED APPLICATION(S)

This application claims the benefit of the following Indian Provisional Application 201941004270 filed Feb. 4, 2019 and the following U.S. Provisional Application No. 62/826,102 filed Mar. 29, 2019, all of which are incorporated herein by reference in their entirety.

TECHNICAL FIELD

This invention relates generally to quality assessment of produce.

BACKGROUND

Generally, fresh vegetables and fruits are manually sorted by retail workers at a facility. Based on the assortment, some fresh vegetables and fruits are destined for retail sale and others are grouped as unsellable.

BRIEF DESCRIPTION OF THE DRAWINGS

Disclosed herein are embodiments of systems, apparatuses and methods pertaining to assessing quality of produce at a facility. This description includes drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various embodiments, systems, apparatuses and methods are provided herein useful for assessing quality of produce at a facility. In some embodiments, there is provided a system including a produce assessment station configured to provide a staging area to determine a quality classification of a target produce. By one approach, the produce assessment station may include a fixed surface and a rotatable base disposed on the fixed surface. In one configuration, the rotatable base may rotate on an axis and secure the target produce when on the rotatable base. Alternatively or in addition to, the produce assessment station may include a first arm coupled to the fixed surface and may include a microphone. Alternatively or in addition to, the produce assessment station may include a second arm including a tapping device. Alternatively or in addition to, the produce assessment station may include a local control circuit. By one approach, the local control circuit may control and couple to the rotatable base, the first arm, and/or the second arm. In one configuration, the local control circuit may rotate the rotatable base at a particular angle and at a particular time interval. Alternatively or in addition to, the local control circuit may receive audio data from the microphone. In one example, the audio data may correspond to sound created by the tapping device when the tapping device make a contact with the target produce.

By one approach, the system may include a plurality of sensors coupled to the local control circuit. In one example, each of the plurality of sensors may capture one or more images of the target produce at different side view of the target produce while on the rotatable base. In another example, each sensor may provide the one or more images to the local control circuit. Alternatively or in addition to, the system may include a portable device wirelessly coupled to the local control circuit. By one approach, the portable device may provide a signal to the local control circuit to initiate the quality classification of the target produce.

In some embodiments, there is provided a method for assessing quality of produce at a facility including rotating, by a local control circuit of a produce assessment station, a rotatable base at a particular angle and at a particular time interval. For example, the produce assessment station may provide a staging area to determine a quality classification of a target produce. In one configuration, the produce assessment station may include a fixed surface and the rotatable base disposed on the fixed surface. By one approach, the rotatable base may rotate on an axis and secure the target produce when on the rotatable base. In another configuration, the produce assessment station may include a first arm coupled to the fixed surface. In one example, the first arm may include a microphone. In another configuration, the produce assessment station may include a second arm coupled to the fixed surface. In one example, the second arm may include a tapping device. In another configuration, the produce assessment station may include the local control circuit configured to control and couple to the rotatable base, the first arm, and/or the second arm. In some implementation, the method may include initiating, by the local control circuit, the tapping device to tap the target produce. Alternatively or in addition to, the method may include initiating, by the local control circuit, at least one of a plurality of sensors associated with the produce assessment station to capture one or more images of the target produce. Alternatively or in addition to, the method may include receiving, by the local control circuit, audio data from the microphone. By one approach, the audio data may correspond to sound created by the tapping device when the tapping device make a contact with the target produce.

Figure 1:
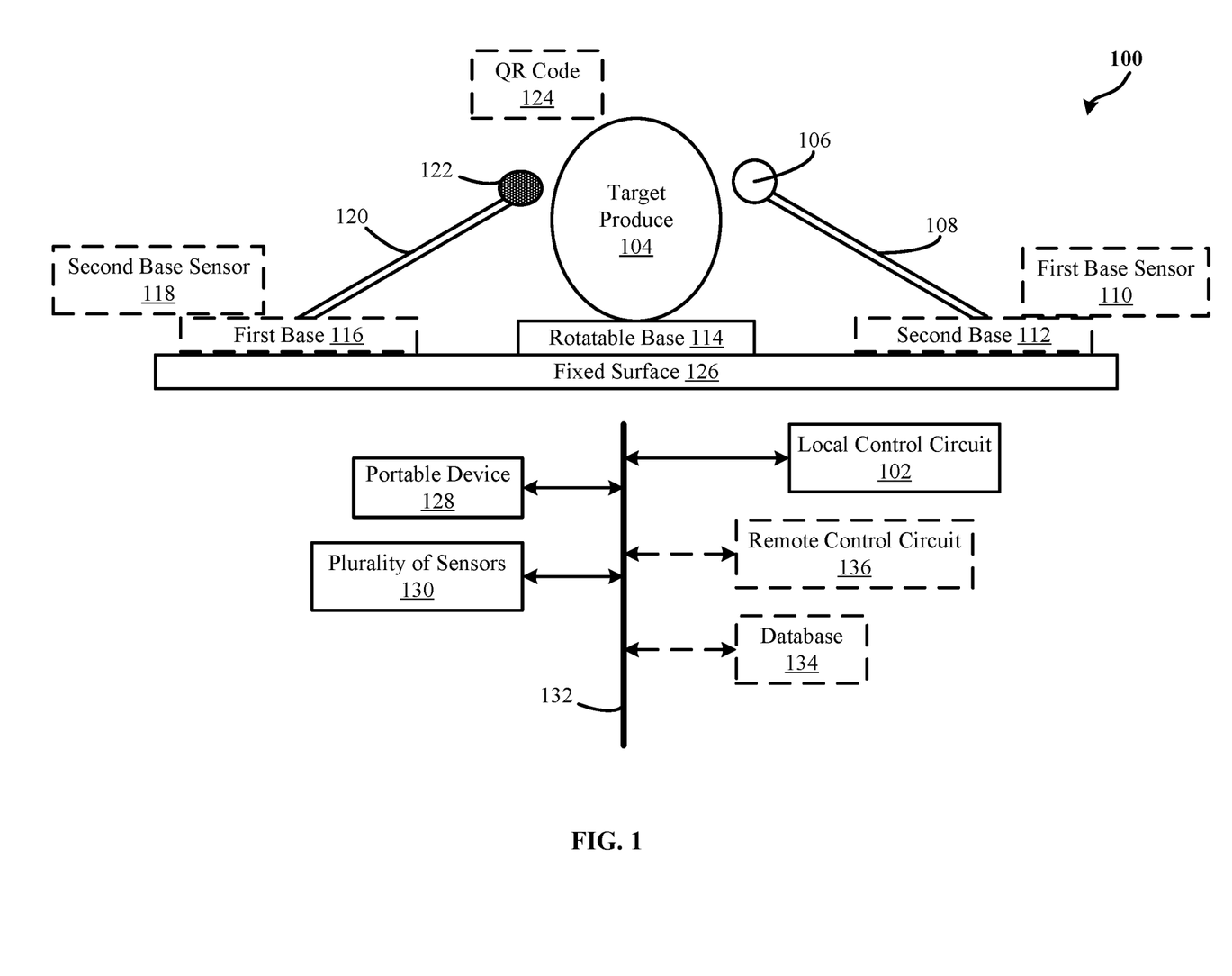
FIG. 1 is a schematic illustration of an exemplary system for assessing quality of produce at a facility in accordance with some embodiments.

To illustrate, FIGS. 1 through 5 are described below. FIG. 1 illustrates an exemplary system 100 for assessing quality of produce at a facility in accordance with some embodiments. The system 100 includes a produce assessment station. By one approach, the produce assessment station may provide a staging area to determine a quality classification of a target produce 104. For example, the classification of a quality of the target produce 104 may be based on at least one of a degree of ripeness (e.g., ripe overripe, unripe, etc.) and/or internal defects. By one approach, the internal defects may include a hollow heart, an internal bruise, and a second growth. In another example, scorability of a target produce 104 may be used in part to determine a quality classification of the target produce 104 in accordance with an industry standard and/or a governmental standard, such as United States Department of Agriculture (USDA), for example. In an illustrative non-limiting example, the quality classification may be based on a plurality of grades as defined by the standards promulgated by the USDA that is particular to the target produce 104. For example, the quality classification may be based at least on the external and/or internal characteristics and/or scorability of the target produce 104. By one approach, the scorability may be associated with and/or based on a determination of a magnitude of internal defects associated with the target produce 104. By another approach, a produce may comprise fruits and/or vegetables. As such, the target produce 104 may comprise a fruit or a vegetable. In one scenario, the target produce 104 may include watermelon, cantaloupe, honeydew, and/or the like.

In some embodiments, the produce assessment station may include a fixed surface 126 and a rotatable base 114 disposed on the fixed surface 126. By one approach, the rotatable base 114 may rotate on an axis and secure the target produce 104 when on the rotatable base 114 such that when the target produce 104 is rotated, the rotatable base 114 keeps the target produce 104 in place. Alternatively or in addition to, the produce assessment station may include a first arm 120 coupled to the fixed surface 126. By one approach, the first arm 120 may include a microphone 122. For example, the first arm 120 may include a robotic arm having an audio receiver (e.g., the microphone 122) attached to one of its end. In another example, the audio receiver may be integrated with the robotic arm. In yet another example, the first arm 120 may include a plurality of material components and/or electrical components assembled together to provide an ability to move the microphone 122 towards and/or away from the target produce 104 and/or move the microphone 122 side to side, up and/or down relative to the target produce 104. In one implementation, the first arm 120 may be coupled to the fixed surface 126 via a first base 116. By one approach, the first base 116 may be movably mounted on the fixed surface 126. In such an approach, the first base 116 may include a second base sensor 118 that may provide sensor data associated with a second distance data between the first base 116 and the target produce 104. In some configuration, the first arm 120 may include the second base sensor 118. In yet another configuration, the first arm 120 and/or the first base 116 may include one or more second base sensors 118 used to ensure that a particular and/or predetermined threshold distance is maintained between the microphone 122 and the target produce 104.

By another approach, the produce assessment station may include a second arm 108. In one configuration, the second arm 108 may include a tapping device 106. For example, the second arm 108 may include a robotic arm having the tapping device 106 attached to one of its end. For example, the tapping device 106 may include a hammer head, a rounded shape material, and/or any material and/or shaped components capable of hitting the target produce 104 without puncturing and/or breaking a surface of the target produce 104. In some scenarios, the tapping device 106 may be integrated with the robotic arm. In yet another example, the second arm 108 may include a plurality of material components and/or electrical components assembled together to provide an ability to move and/or swing the tapping device 106 towards and/or away from the target produce 104 and/or move the tapping device 106 side to side, up and/or down relative to the target produce 104. In one implementation, the second arm 108 may be coupled to the fixed surface 126 via a second base 112. By one approach, the second base 112 may be movably mounted on the fixed surface 126. In such an approach, the second base 112 may include a first base sensor 110 that may provide sensor data associated with a first distance data between the second base 112 and the target produce 104. In some configuration, the second arm 108 may include the first base sensor 110. In yet another configuration, the second arm 108 and/or the second base 112 may include one or more first base sensors 110 used to ensure that a particular and/or predetermined second threshold distance is maintained between the tapping device 106 and the target produce 104.

In some implementations, the produce assessment station may include a local control circuit 102. For example, the local control circuit 102 may include microcontroller, processor, and/or a distributed computer system including a plurality of computers, servers, processors, and/or controllers, to name a few. By one approach, the local control circuit 102 may control and couple to the rotatable base 114, the first arm 120, and/or the second arm 108. For example, the local control circuit may rotate the rotatable base 114 at a particular angle and at a particular time interval. In an illustrative non-limiting example, the local control circuit may rotate the rotatable base 114 every minute at 45 degrees interval relative to a horizontal axis of the target produce 104 until the target produce 104 has been rotated in a full circle. In another illustrative non-limiting example, the local control circuit 102 may instead rotate the rotatable base 114 at 90 degrees interval relative to a horizontal axis every 30 seconds until the target produce 104 has been rotated in a full circle. In such examples, the local control circuit may rotate the rotatable base 114 at a particular angle and at a particular time interval based on an input from a user and/or based on a predetermined angle and/or a predetermined time interval programmed to the local control circuit 102. By one approach, prior to the rotatable base 114 being rotated by the local control circuit 102, the local control circuit 102 may operate the second arm 108 to tap the target produce 104. In response to the tapping of the target produce 104, the local control circuit 102 may receive audio data from the microphone 122. For example, the audio data may correspond to sound created and/or generated by the tapping device 106 when the tapping device 106 make a contact with the target produce 104.

In some embodiments, the system 100 may include a plurality of sensors 130 coupled to the local control circuit 102 via a communication network 132. By one approach, the communication network 132 may include wireless and/or wired network. In one configuration, the communication network 132 may include Internet, local area network, wide area network, ethernet network, wireless network, WIFI, BLUETOOTH, and/or the like. In some configurations, the plurality of sensors 130 may include optical sensor, cameras, and/or any commercially available sensors capable of providing the local control circuit 102 image data and/or sensor data that is associated with the target produce's 104 external characteristics, such as shape, size, color, visible markings, blemishes, and/or among other external characteristics used to determine quality of the target produce 104. In some implementations, each of the plurality of sensors 130 may capture one or more images of the target produce 104 at different side view of the target produce 104 while on the rotatable base 114. For example, whenever the rotatable base 114 is rotated by the local control circuit 102, the plurality of sensors 130 may capture one or more images of the target produce 104 relative to a particular view at each of the plurality of sensors 130. In another example, the local control circuit 102 may periodically capture one or more images of the target produce 104 at a particular time interval. In response to capturing the one or more images, each of the plurality of sensors 130 may provide the one or more images to the local control circuit 102. In some embodiments, the system 100 may include a portable device 128 wirelessly coupled to the local control circuit 102. For example, the portable device 128 may include a smartphone, a computer, a laptop, a server, a desktop, an iPad, a tablet, and/or the like. By one approach, the portable device 128 may provide a signal to the local control circuit 102 to initiate a quality classification of the target produce 104.

Figure 2:
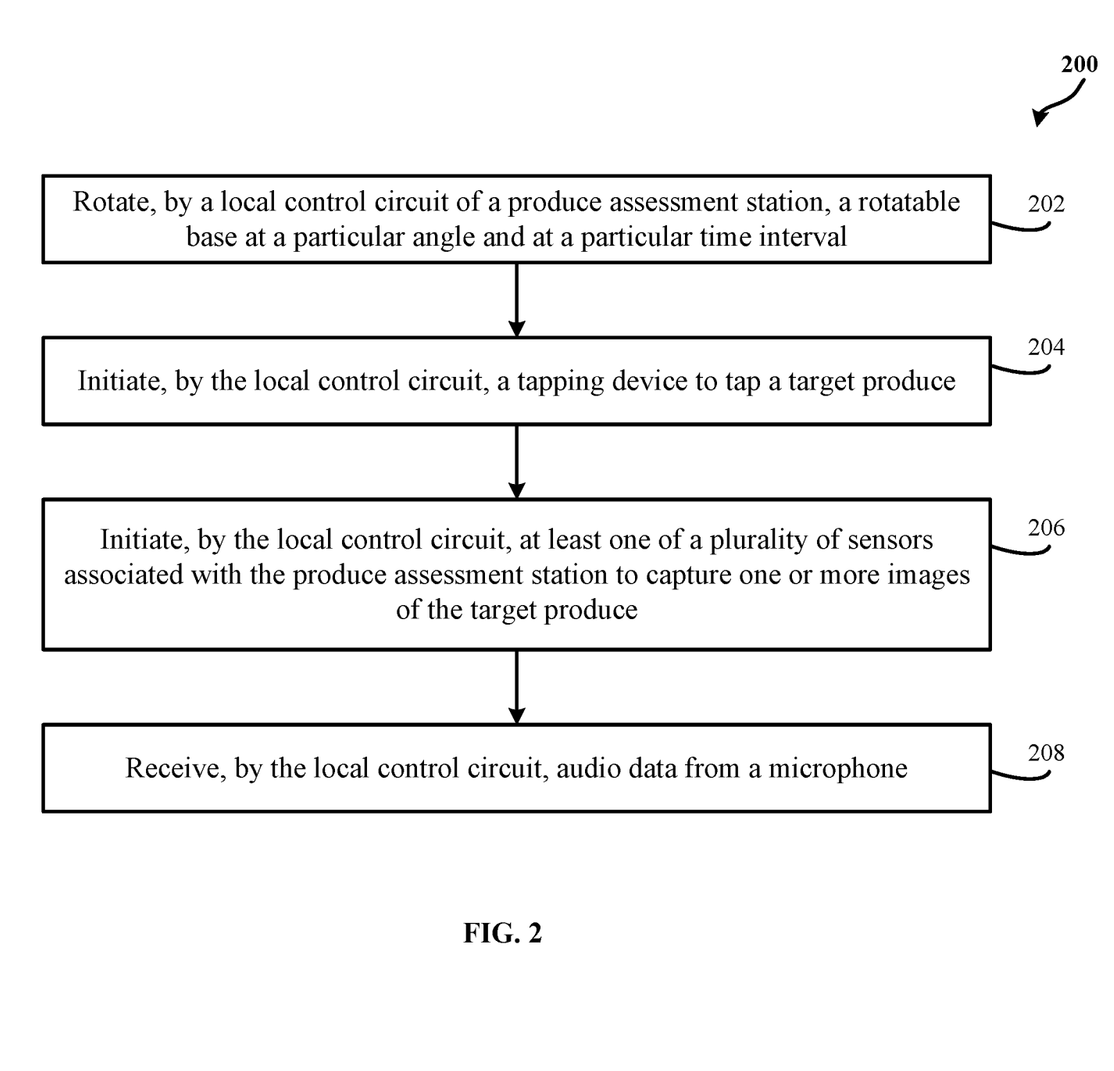
FIG. 2 is an exemplary flow diagram of a system for assessing quality of produce at a facility in accordance with some embodiments.
Figure 3:
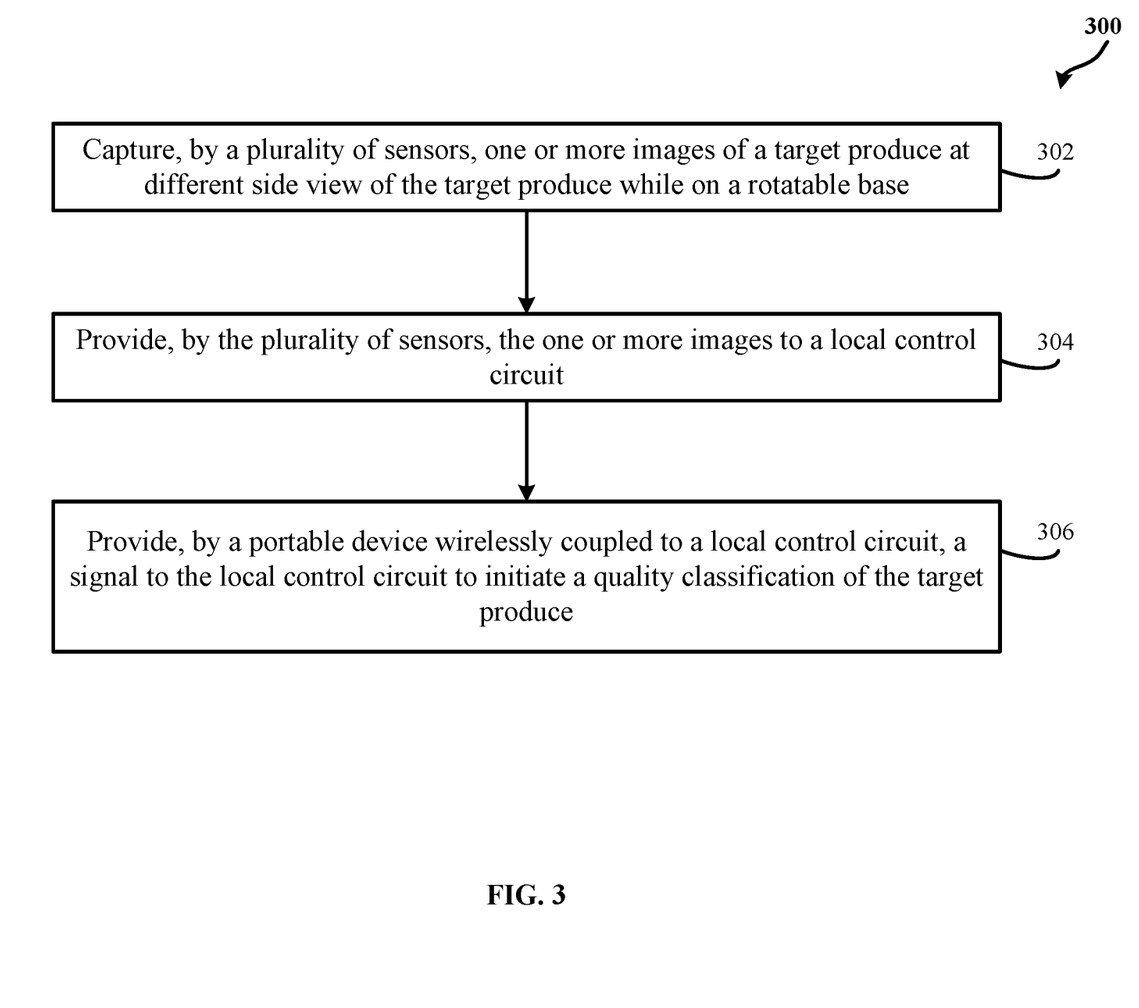
FIG. 3 is another exemplary flow diagram of a system for assessing quality of produce at a facility in accordance with some embodiments.
Figure 4:
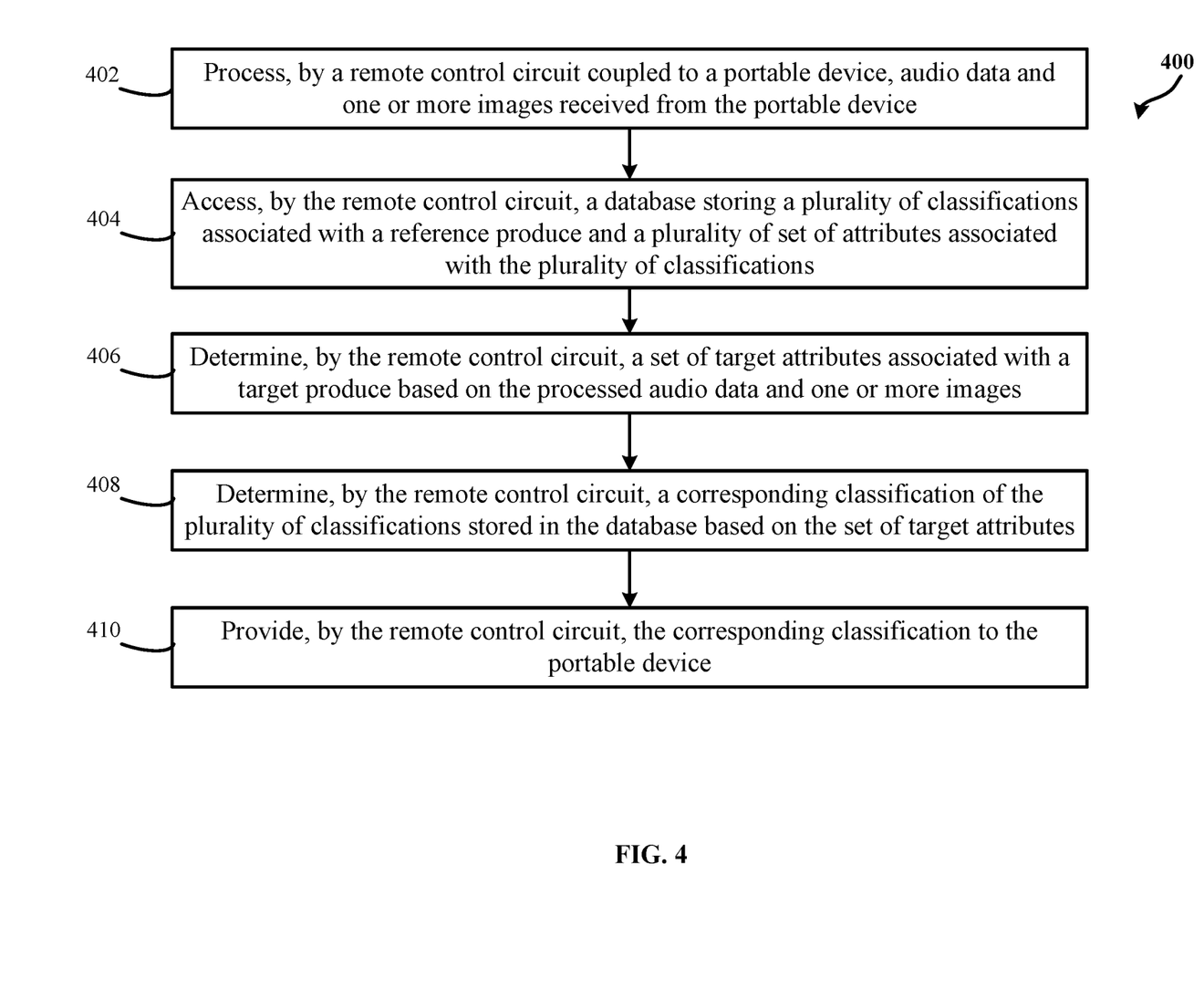
FIG. 4 is another exemplary flow diagram of a system for assessing quality of produce at a facility in accordance with some embodiments.

FIGS. 2-4 are exemplary methods 200, 300, and 400, respectively, for assessing quality of produce at a facility in accordance with some embodiments. FIGS. 2-4 are described below with FIG. 1 to provide an illustrative non-limiting example of a facility (e.g., a distribution center, a retail store, a sorting facility, etc.) receiving a shipment of the target produce 104, for example watermelons. By one approach, the system 100 may assess the quality of each target watermelon in the shipment and subsequently place each target watermelon in a particular group in accordance with the determined classification associated with the target watermelon. For example, when the target watermelon is associated with a particular determined classification, the target watermelon may then be associated with a particular group of a plurality of groups in accordance with an industry standard or based on a governmental established standard (e.g., USDA standard for watermelons). In one scenario, the plurality of groups may include U.S. Fancy, U.S. No. 1, U.S. No. 2, and/or not acceptable, among other types of groupings based on classifications. In another scenario, the plurality of groups may be based on other countries' established industry and/or governmental standards.

By one approach, the target watermelon is placed on the rotatable base 114. In one configuration, the local control circuit 102 may detect the placement of the target watermelon on the rotatable base 114 through one or more presence and/or proximity sensors (not shown) coupled to the local control circuit 102. In one scenario, the local control circuit 102 may initiate a quality classification by rotating the rotatable base 114 at a particular angle and at a particular time interval, at step 202. In another scenario, a user associated with the portable device 128 may provide a user input that triggers the portable device 128 to provide a signal to the local control circuit 102 to initiate the quality classification of the watermelon. In such scenarios, the local control circuit 102 may operate on the second arm 108 to move the tapping device 106 and make contact with the target watermelon, in other words, tap the target watermelon, at step 204. For example, the local control circuit 102 at every particular/predetermined angle and at a particular/predetermined time interval may initiate the tapping device 106 to tap the target produce, for example the watermelon. To illustrate, the watermelon is rotated at 90 degrees interval every minute and tapped prior to the next 90 degrees rotation. By one approach, the local control circuit 102 may continually rotate the rotatable base 114 until the target watermelon has been rotated in a full circle. Alternatively or in addition to, after each rotation and/or prior to the next rotation, the local control circuit 102 may, at step 206, initiate at least one of the plurality of sensors 130 to capture one or more images of the target watermelon, the target produce 104 in this example. In response, the local control circuit 102 may receive the one or more images of the target watermelon. By one approach, the received one or more images may be used to determine a classification to be associated with the target watermelon.

In some implementation, as the target watermelon is rotated by the local control circuit 102, the local control circuit may continually determine a first distance between the second base 112 and the target watermelon based on a distance data received from the first base sensor 110. In response to the determination of the first distance, the local control circuit 102 may move the second base 112 relative to the target watermelon by a second distance that substantially maintains a first predetermined distance between the second base 112 and the target watermelon. As such, the tapping device 106 does not make contact with the target watermelon while the target watermelon is being rotated. For example, the first predetermined distance may comprise any value and/or range of distance in English or Metric units that enable the system 100 to perform the quality assessment within a particular time interval (e.g., the system 100 may be configured to complete a quality assessment for every target produce 104 every two minutes or any time interval predetermined prior to the initiation of the quality assessment).

Alternatively or in addition to, in response to the tapping device 106 tapping the target watermelon, the local control circuit 102 may receive audio data from the microphone 122, at step 208. By one approach, the audio data may comprise sound created by the tapping device 106 when the tapping device 106 make a contact with the target watermelon. In one configuration, as the target watermelon is rotated by the local control circuit 102, the local control circuit 102 may continually determine a third distance between the first base 116 and the target watermelon based on a second distance data received from the second base sensor 118. In response to the determination of the third distance, the local control circuit 102 may move the first base 116 relative to the target watermelon by a fourth distance that substantially maintains a second predetermined distance between the first base 116 and the target watermelon. As such, the microphone 122 does not make contact with the target watermelon while the target watermelon is being rotated. For example, the second predetermined distance may comprise any value and/or range of distance in English or Metric units that enable the system 100 to perform the quality assessment within a particular time interval (e.g., the system 100 may be configured to complete a quality assessment for every target produce 104 every two minutes or any time interval predetermined prior to the initiation of the quality assessment). In some implementations, the first and second base sensors may include a distance sensor, a proximity sensor, laser sensor, optical sensor, and/or any sensors capable of providing sensor data used to determine distance between two objects and/or between the sensor(s) and an object.

In some implementations, in between rotation of the target watermelon, the plurality of sensors 130 may, at step 302, capture one or more images of the target watermelon at different side view of the target watermelon while on the rotatable base 114. By one approach, the plurality of sensors

130 may provide the one or more images to the local control circuit 102, at step 304. By another approach, the plurality of sensors 130 may initially capture the one or more images of the target watermelon prior to initiating a quality classification of the target watermelon. In response, the portable device 128 may provide a signal to the local control circuit 102 via the communication network 132 (e.g., a wireless communication network) to initiate the quality classification of the target watermelon, at step 306. Although, the description herein may describe a watermelon, it is understood by those ordinary skilled in the art that the system 100 for assessing quality of produce at a facility is applicable to other kinds of fruits and/or vegetables.

In some embodiments, the system 100 may include a database 134. For example, the database 134 may include one or more memory storage devices including Random Access Memory (RAM), Read Only Memory, (ROM), external and/or internal hard drives, solid state drives, network attached storage (NAS), thumb drives, flash drives, optical drives, and/or cloud storage, among other types of electronic devices capable of storing electronic data. By one approach, the database 134 may store a plurality of classifications associated with a reference produce and a plurality of set of attributes associated with the plurality of classifications. In one configuration, each classification of the plurality of classifications may be associated with a particular set of attributes of the plurality of set of attributes. In such configuration, the particular set of attributes may be associated with a particular classification of the reference produce. Alternatively or in addition to, the attributes may include a digital representation of a particular sound (e.g., Mel-frequency cepstral (MFCC) coefficients, among other types of digital representations of sounds) created by the reference produce having the particular classification when tapped by the tapping device 106, geographical data, color of ground spot, weight, and/or density associated with the reference produce having the particular classification. In another configuration, the database 134 may store a plurality of models of a reference produce where each model corresponds to a particular mathematical representation of a particular classification of a plurality of classifications having a particular scorability of a plurality of scorabilities and/or a particular set of attributes of a plurality of attributes that are associated with a particular digital representation of a particular sound created by the reference produce when the reference produce is tapped by the tapping device 106. By one approach, the plurality of attributes may include geographical data, color of a ground spot, weight, volume, and/or density associated with the reference produce. For example, the geographical data may include geographic location, harvest date, weather, originating farm, and transport temperature from the originating farm to a facility. In one scenario, the temperature information of the target produce 104 may be obtained through sensor data provided by a plurality of temperature sensors distributed at a supplier's facility, a transportation vehicle, and/or a destination facility. In such a scenario, the temperature information is encoded and/or associated with a Quick Response (QR) code 124 associated the target produce 104. In another scenario, the geographical data may be associated with the QR code 124 associated the target produce 104. By one approach, the QR code 124 may be attached to a surface of the target produce 104. In an illustrative non-limiting example, one of the plurality of sensors 130 may capture an image of the QR code 124. By one approach, upon receiving the image including the captured QR code 124, the local control circuit 102 and/or a remote control circuit 136 may process the image using commercially available data processing techniques, methods, and/or machine learning algorithms. Upon processing the image, the local control circuit 102 and/or the remote control circuit 136 may determine the QR code 124. By one approach, the local control circuit 102 and/or the remote control circuit 136 may subsequently access a weather database via a commercially available weather application program interface (API) to obtain weather information associated with the target produce 104. Alternatively or in addition to, the plurality of attributes may include a degree of ripeness (e.g., ripe, unripe, overripe, etc.), internal defects, external defects (e.g., rindworms), and/or scorability. In some implementations, the plurality of models may be based on models output by one or more machine learning algorithms. In some implementations, a corresponding classification of the target produce 104 may be used by a user of the portable device 128 to group the target produce 104 with other produce having the same corresponding classification at a facility associated with a retail store. For example, one or more resulting groups may either be accepted or rejected by the user based on the corresponding classification. In an illustrative non-limiting example, the target produce 104 may comprise a target watermelon. By one approach, a plurality of classifications may be based on at least one of a degree of ripeness (e.g., ripe, unripe, overripe, etc.), internal defects, and scorability. By another approach, the plurality of classifications may include of the degree of ripeness (e.g., ripe, unripe, overripe, etc.) and/or internal defects. In one scenario, the internal defects may include a hollow heart, an internal bruise, and/or a second growth. In some implementations, the scorability of the target watermelon may be based on a magnitude of the internal defects and/or a length of its internal bruise. As such, based on the particular digital representation of the audio data received by the local control circuit 102 when the target watermelon is tapped by the tapping device 106, the local control circuit 102 and/or the remote control circuit 136 may determine a particular scorability associated with the particular digital representation of the audio data based on the plurality of models stored in the database 134. For example, the local control circuit 102 and/or the remote control circuit 136 may determine which one of the plurality of models includes, represents, and/or associated with the particular digital representation of the audio data received by the local control circuit 102 when the target watermelon is tapped by the tapping device 106. In response, based on the determined model, the local control circuit 102 and/or the remote control circuit 136 may determine and/or predict the particular scorability associated with the target watermelon. In some scenarios, the scorability may include damage, serious damage, acceptable, to name a few. Alternatively or in addition to, the local control circuit 102 and/or the remote control circuit 136 may, based on the determined model, determine and/or predict a corresponding classification associated with the target watermelon. For example, the local control circuit 102 and/or the remote control circuit 136 may determine a corresponding model based on a set of attributes particular to the target watermelon and a digital representation of a sound created by the target watermelon when the target watermelon is tapped by the tapping device 106. In such example, the local control circuit 102 and/or the remote control circuit 136 in cooperation with the database 134 may determine which one of the plurality of models substantially corresponds to a reference watermelon having substantially similar set of attributes and digital representation of sound as those of the target watermelon. In response, based on the determined model, the local control circuit 102 and/or the remote control circuit 136 may determine and/or predict a classification based on and/or corresponding to the determined model. In response to the determination of the corresponding classification associated with the target watermelon, the system 100 may automatically sort the classified watermelon into a particular group having the same determined classification. As such, after the target watermelons are sorted into groups based on their corresponding classifications, the local control circuit 102 and/or the remote control circuit 136 may send a message to the portable device 128 that the quality assessment associated with the facility has been completed. By one approach, a user may reject a particular lot of the received shipment of watermelons based on the determined classification and/or the resulting group that target watermelons are sorted to. In some embodiments, the local control circuit 102 and/or the remote control circuit 136 may use at least in part a machine learning algorithm, processing, and/or techniques to determine a corresponding model to use and a corresponding classification associated with the target watermelon.

In some embodiments, the remote control circuit 136 may couple to the portable device 128. By one approach, the remote control circuit 136 may process the audio data and the one or more images received from the portable device 128, at step 402. In one example, the local control circuit 102 may provide audio data and/or one or more images received from the portable device 128. Alternatively or in addition to, the remote control circuit 136 may access the database 134 storing a plurality of classifications associated with a reference produce and a plurality of set of attributes associated with the plurality of classifications, at step 404. Alternatively or in addition to, the remote control circuit 136 may determine a set of target attributes associated with the target produce 104 based on the audio data and the one or more images processed by the remote control circuit 136, at step 406. In one example, processing of the audio data and the one or more images may be based on one or more commercially available data processing techniques, methods, and/or machine learning algorithms. In another example, the plurality of sensors 130, for example cameras, are distributed in proximity to the produce assessment station so that a plurality of images of the target produce 104 may be captured at different angles of the target produce 104. Alternatively or in addition to, the remote control circuit 136 may determine a corresponding classification associated with the target produce 104 based on the plurality of classifications stored in the database 134 based on the set of target attributes, at step 408. Alternatively or in addition to, the remote control circuit 136 may provide the corresponding classification to the portable device 128, at step 410. By one approach, the portable device 128 may display the corresponding classification to a display unit (not shown) associated with the portable device 128. In some embodiments, the functions described herein for the local control circuits 102 maybe solely performed by the remote control circuit 136. Alternatively, in some embodiments, the functions described herein for the remote control circuit 136 maybe solely performed by the local control circuits 102. By one approach, the remote control circuit 136 may include microcontroller, processor, and/or a distributed computer system including a plurality of computers, servers, processors, and/or controllers, to name a few.

Figure 5:
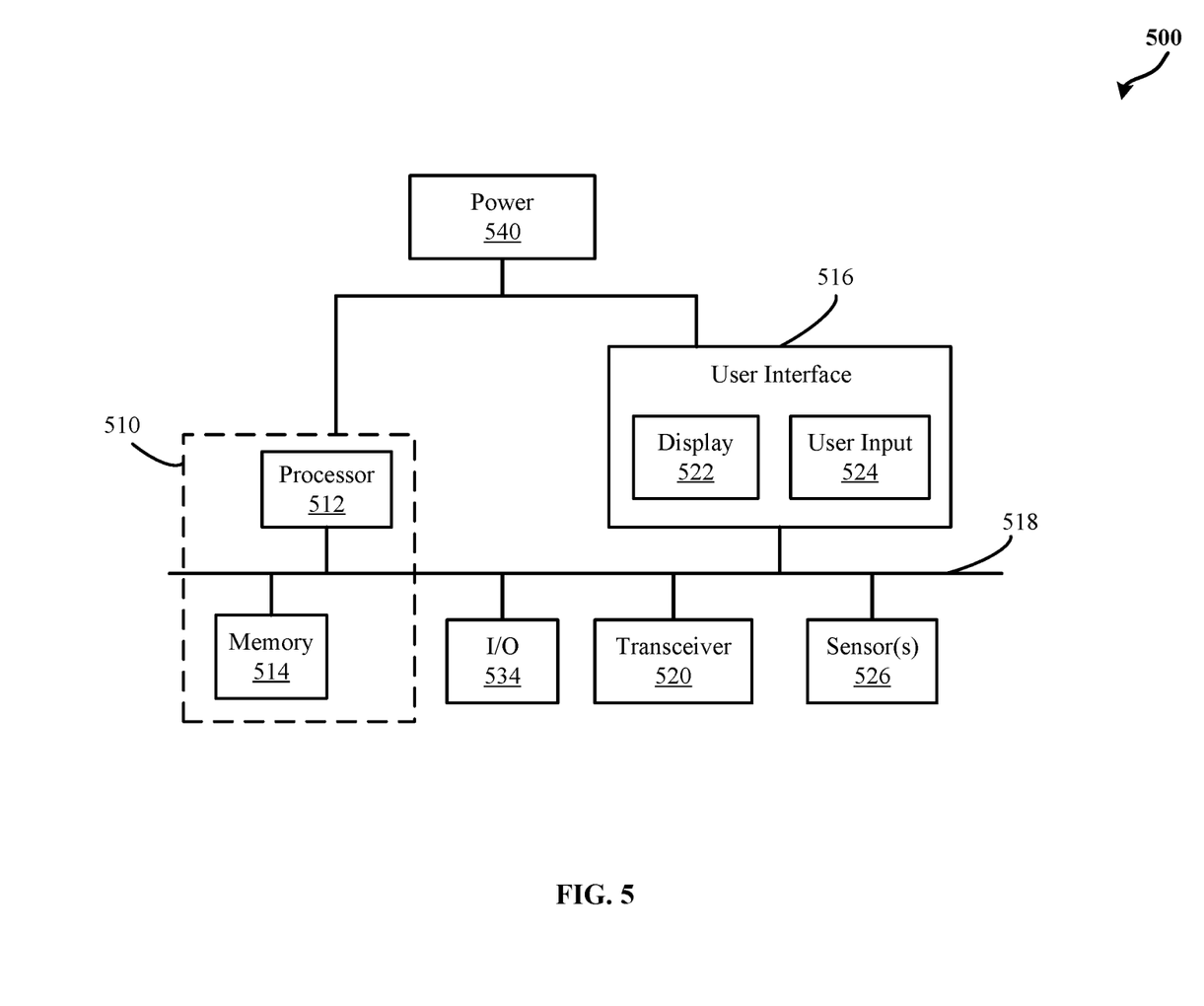
FIG. 5 illustrates an exemplary system for use in implementing systems, apparatuses, devices, methods, techniques, and the like in assessing quality of produce at a facility in accordance with several embodiments.

Further, the circuits, circuitry, systems, devices, processes, methods, techniques, functionality, services, servers, sources and the like described herein may be utilized, implemented and/or run on many different types of devices and/or systems. FIG. 5 illustrates an exemplary system 500 that may be used for implementing any of the components, circuits, circuitry, systems, functionality, apparatuses, processes, or devices of the system 100 of FIG. 1, the method 200 of FIG. 2, the method 300 of FIG. 3, the method 400 of FIG. 4, and/or other above or below mentioned systems or devices, or parts of such circuits, circuitry, functionality, systems, apparatuses, processes, or devices. For example, the system 500 may be used to implement some or all of the system for assessing quality of produce at a facility, the local control circuit 102, the produce assessment station, the plurality of sensors 130, the portable device 128, the database 134, the remote control circuit 136, the first base sensor 110, the second base sensor 118, the first arm 120, the second arm 108, the microphone 122, the communication network 132, and/or other such components, circuitry, functionality and/or devices. However, the use of the system 500 or any portion thereof is certainly not required.

By way of example, the system 500 may comprise a processor module (or a control circuit) 512, memory 514, and one or more communication links, paths, buses or the like 518. Some embodiments may include one or more user interfaces 516, and/or one or more internal and/or external power sources or supplies 540. The control circuit 512 can be implemented through one or more processors, microprocessors, central processing unit, logic, local digital storage, firmware, software, and/or other control hardware and/or software, and may be used to execute or assist in executing the steps of the processes, methods, functionality and techniques described herein, and control various communications, decisions, programs, content, listings, services, interfaces, logging, reporting, etc. Further, in some embodiments, the control circuit 512 can be part of control circuitry and/or a control system 510, which may be implemented through one or more processors with access to one or more memory 514 that can store instructions, code and the like that is implemented by the control circuit and/or processors to implement intended functionality. In some applications, the control circuit and/or memory may be distributed over a communications network (e.g., LAN, WAN, Internet) providing distributed and/or redundant processing and functionality. Again, the system 500 may be used to implement one or more of the above or below, or parts of, components, circuits, systems, processes and the like. For example, the system 500 may implement the system 100 for assessing quality of produce at a facility with the local control circuit 102 being the control circuit 512.

The user interface 516 can allow a user to interact with the system 500 and receive information through the system. In some instances, the user interface 516 includes a display 522 and/or one or more user inputs 524, such as buttons, touch screen, track ball, keyboard, mouse, etc., which can be part of or wired or wirelessly coupled with the system 500. Typically, the system 500 further includes one or more communication interfaces, ports, transceivers 520 and the like allowing the system 500 to communicate over a communication bus, a distributed computer and/or communication network (e.g., a local area network (LAN), the Internet, wide area network (WAN), etc.), communication link 518, other networks or communication channels with other devices and/or other such communications or combination of two or more of such communication methods. Further the transceiver 520 can be configured for wired, wireless, optical, fiber optical cable, satellite, or other such communication configurations or combinations of two or more of such communications. Some embodiments include one or more input/output (I/O) interface 534 that allow one or more devices to couple with the system 500. The I/O interface can be substantially any relevant port or combinations of ports, such as but not limited to USB, Ethernet, or other such ports. The I/O interface 534 can be configured to allow wired and/or wireless communication coupling to external components. For example, the I/O interface can provide wired communication and/or wireless communication (e.g., Wi-Fi, Bluetooth, cellular, RF, and/or other such wireless communication), and in some instances may include any known wired and/or wireless interfacing device, circuit and/or connecting device, such as but not limited to one or more transmitters, receivers, transceivers, or combination of two or more of such devices.

In some embodiments, the system may include one or more sensors 526 to provide information to the system and/or sensor information that is communicated to another component, such as the central control system, a portable retail container, a vehicle associated with the portable retail container, etc. The sensors can include substantially any relevant sensor, such as temperature sensors, distance measurement sensors (e.g., optical units, sound/ultrasound units, etc.), optical based scanning sensors to sense and read optical patterns (e.g., bar codes), radio frequency identification (RFID) tag reader sensors capable of reading RFID tags in proximity to the sensor, and other such sensors. The foregoing examples are intended to be illustrative and are not intended to convey an exhaustive listing of all possible sensors. Instead, it will be understood that these teachings will accommodate sensing any of a wide variety of circumstances in a given application setting.

The system 500 comprises an example of a control and/or processor-based system with the control circuit 512. Again, the control circuit 512 can be implemented through one or more processors, controllers, central processing units, logic, software and the like. Further, in some implementations the control circuit 512 may provide multiprocessor functionality.

The memory 514, which can be accessed by the control circuit 512, typically includes one or more processor readable and/or computer readable media accessed by at least the control circuit 512, and can include volatile and/or nonvolatile media, such as RAM, ROM, EEPROM, flash memory and/or other memory technology. Further, the memory 514 is shown as internal to the control system 510; however, the memory 514 can be internal, external or a combination of internal and external memory. Similarly, some or all of the memory 514 can be internal, external or a combination of internal and external memory of the control circuit 512. The external memory can be substantially any relevant memory such as, but not limited to, solid-state storage devices or drives, hard drive, one or more of universal serial bus (USB) stick or drive, flash memory secure digital (SD) card, other memory cards, and other such memory or combinations of two or more of such memory, and some or all of the memory may be distributed at multiple locations over the computer network. The memory 514 can store code, software, executables, scripts, data, content, lists, programming, programs, log or history data, user information, customer information, product information, and the like. While FIG. 5 illustrates the various components being coupled together via a bus, it is understood that the various components may actually be coupled to the control circuit and/or one or more other components directly.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A system for assessing quality of produce at a facility comprising:
    a produce assessment station configured to provide a staging area to determine a quality classification of a target produce and comprising:
        a fixed surface;
        a rotatable base disposed on the fixed surface and configured to:
            rotate on an axis; and
            secure the target produce when on the rotatable base;
        a first arm coupled to the fixed surface and comprising a microphone;
        a second arm comprising a tapping device; and
        a local control circuit configured to control and couple to the rotatable base, the
            first arm, and the second arm, the local control circuit configured to:
            periodically rotate the rotatable base at a particular angle and at a particular time interval in multiple rotations until the target produce has been rotated in substantially a full circle, wherein the particular angle and the particular time interval are programmed to the local control circuit to automatically rotate the rotatable base periodically; and
            receive audio data from the microphone, wherein the audio data corresponds to sound created by the tapping device contacting the target produce at each periodic rotation;
    a plurality of sensors coupled to the local control circuit, wherein each of the plurality of sensors is configured to:
        capture one or more images of the target produce at different side view of the target produce while on the rotatable base; and
        provide the one or more images to the local control circuit; and
    a portable device wirelessly coupled to the local control circuit, the portable device configured to provide a signal to the local control circuit to initiate the quality classification of the target produce.

2. The system of claim 1, further comprising:
    a database storing a plurality of classifications associated with a reference produce and a plurality of set of attributes associated with the plurality of classifications, wherein each classification of the plurality of classifications is associated with a particular set of attributes of the plurality of set of attributes, wherein the particular set of attributes is associated with a particular classification of the reference produce; and wherein the attributes comprise a digital representation of a particular sound created by the reference produce being tapped by the tapping device, geographical data, color of a ground spot, weight, and density associated with the reference produce having the particular classification; and
    a remote control circuit coupled to the portable device, the remote control circuit configured to:
        process the audio data and the one or more images received from the portable device;
        determine a set of target attributes associated with the target produce based on the processed audio data and one or more images;

determine a corresponding classification of the plurality of classifications stored in the database based on the set of target attributes; and provide the corresponding classification to the portable device.

3. The system of claim 2, wherein the corresponding classification of the target produce is used by a user of the portable device to group the target produce with other produce having the same corresponding classification at a facility associated with a retail store, wherein one or more resulting groups of produce are accepted or rejected by the user, and wherein classifications of the one or more resulting groups of produce is based on a quality assessment associated with the facility.

4. The system of claim 2, wherein the target produce comprises a watermelon, wherein the plurality of classifications may be based on at least one of a degree of ripeness, scorability, and internal defects, wherein the internal defects comprise a hollow heart, an internal bruise, and a second growth, and wherein the scorability is associated with a magnitude of the internal defects.

5. The system of claim 2, wherein the geographical data comprise geographic location, harvest date, weather, originating farm, and transport temperature from the originating farm to a facility.

6. The system of claim 5, wherein the geographical data is associated with a Quick Response (QR) code associated the target produce.

7. The system of claim 1, wherein the local control circuit is further configured to continually rotate the rotatable base until the target produce has been rotated in a full circle.

8. The system of claim 1, further comprising:
a first base movably mounted on the fixed surface, wherein the first arm is coupled to the fixed surface via the first base; and
a second base movably mounted on the fixed surface, wherein the second arm is coupled to the fixed surface via the second base.

9. The system of claim 8, wherein the second base comprises a first base sensor configured to provide a first distance data between the second base and the target produce, wherein the local control circuit is further configured to:
determine a first distance between the second base and the target produce based on the first distance data from the first base sensor; and
in response to the determination of the first distance, move the second base relative to the target produce by a second distance that substantially maintains a first predetermined distance between the second base and the target produce.

10. The system of claim 8, wherein the first base comprise a second base sensor configured to provide a second distance data between the first base and the target produce, wherein the local control circuit is further configured to:
determine a third distance between the first base and the target produce based on the second distance data from the second base sensor; and
in response to the determination of the third distance, move the first base relative to the target produce by a fourth distance that substantially maintains a second predetermined distance between the first base and the target produce.

11. The system of claim 1, wherein the local control circuit at the particular angle and at the particular time interval is further configured to:

initiate the tapping device to tap the target produce; and
initiate at least one of the plurality of sensors to capture the one or more images of the target produce.

12. A method for assessing quality of produce at a facility comprising:
rotating periodically, by a local control circuit of a produce assessment station, a rotatable base at a particular angle and at a particular time interval in multiple rotations until a target produce has been rotated in substantially a full circle, wherein the particular angle and the particular time interval are programmed to the local control circuit to automatically rotate the rotatable base periodically, and wherein the produce assessment station is configured to provide a staging area to determine a quality classification of the target produce and comprises:
a fixed surface;
the rotatable base disposed on the fixed surface and configured to: rotate on an axis;
and secure the target produce on the rotatable base;
a first arm coupled to the fixed surface and comprising a microphone;
a second arm coupled to the fixed surface and comprising a tapping device; and
the local control circuit configured to control and couple to the rotatable base, the first arm, and the second arm;
initiating, by the local control circuit, the tapping device to tap the target produce;
initiating, by the local control circuit, at least one of a plurality of sensors associated with the produce assessment station to capture one or more images of the target produce; and
receiving, by the local control circuit, audio data from the microphone, wherein the audio data corresponds to sound created by the tapping device contacting the target produce at each periodic rotation.

13. The method of claim 12, further comprising:
capturing, by the plurality of sensors, the one or more images of the target produce at different side view of the target produce while on the rotatable base;
providing, by the plurality of sensors, the one or more images to the local control circuit; and
providing, by a portable device wirelessly coupled to the local control circuit, a signal to the local control circuit to initiate the quality classification of the target produce.

14. The method of claim 12, further comprising:
processing, by a remote control circuit coupled to a portable device, the audio data and the one or more images received from the portable device;
accessing, by the remote control circuit, a database storing a plurality of classifications associated with a reference produce and a plurality of a set of attributes associated with the plurality of classifications, wherein each classification of the plurality of classifications is associated with a particular set of attributes of the plurality of a set of attributes, wherein the particular set of attributes is associated with a particular classification of the reference produce; and wherein the attributes comprise a digital representation of a particular sound created by the reference produce being tapped by the tapping device, geographical data, color of a ground spot, weight, and density associated with the reference produce having the particular classification;

determining, by the remote control circuit, a set of target attributes associated with the target produce based on the processed audio data and one or more images;

determining, by the remote control circuit, a corresponding classification of the plurality of classifications stored in the database based on the set of target attributes; and providing, by the remote control circuit, the corresponding classification to the portable device.

15. The method of claim 14, wherein the corresponding classification of the target produce is used by a user of the portable device to group the target produce with other produce having the same corresponding classification at a facility associated with a retail store, wherein one or more resulting groups of produce are accepted or rejected by the user, and wherein classifications of the one or more resulting groups of produce is based on a quality assessment associated with the facility.

16. The method of claim 14, wherein the target produce comprises a watermelon, wherein the plurality of classifications may be based on at least one of a degree of ripeness, scorability, and internal defects, wherein the internal defects comprise hollow heart, internal bruise, and second growth, and wherein the scorability is associated with a magnitude of the internal defects.

17. The method of claim 14, wherein the geographical data comprise geographic location, harvest date, weather, originating farm, and transport temperature from the originating farm to a facility.

18. The method of claim 17, wherein the geographical data is associated with a Quick Response (QR) code associated the target produce.

19. The method of claim 12, further comprising continually rotating, by the local control circuit, the rotatable base until the target produce has been rotated in a full circle.

20. The method of claim 12, further comprising:

determining, by the local control circuit, a first distance between a second base and the target produce based on a first distance data from a first base sensor of the second base, wherein the first base sensor is configured to provide the first distance data between the second base and the target produce, wherein the produce assessment station further comprises the second base movably mounted on the fixed surface, and wherein the second arm is coupled to the fixed surface via the second base; and in response to the determining of the first distance, moving, by the local control circuit, the second base relative to the target produce by a second distance that substantially maintains a first predetermined distance between the second base and the target produce.

21. The method of claim 12, further comprising:

determining, by the local control circuit, a third distance between a first base and the target produce based on a second distance data from a second base sensor of the first base, wherein the second base sensor is configured to provide the second distance data between the first base and the target produce, wherein the produce assessment station further comprises the first base movably mounted on the fixed surface, and wherein the second arm is coupled to the fixed surface via the second base; and in response to the determining of the third distance, moving, by the local control circuit, the first base relative to the target produce by a fourth distance that substantially maintains a second predetermined distance between the first base and the target produce.

22. The method of claim 13, wherein each sensor of the plurality of sensors captures a side view different from side views captured by other sensors of the plurality of sensors.

23. The method of claim 22, wherein the one or more images are captured at each periodic rotation.

* * * * *

UNITED STATES PATENT AND TRADEMARK OFFICE
CERTIFICATE OF CORRECTION

PATENT NO. : 11,113,808 B2
APPLICATION NO. : 16/745195
DATED : September 7, 2021
INVENTOR(S) : Mangesh N. Kulkarni Wadhonkar et al.

It is certified that error appears in the above-identified patent and that said Letters Patent is hereby corrected as shown below:

On the Title Page

Column 2, (56) References Cited, OTHER PUBLICATIONS, delete "retrived" and insert --retrieved--, therefor.

In the Claims

Claim 1, Column 12, Line 15, after "produce", delete "when".
Claim 6, Column 13, Line 29, before "the", insert --with--.
Claim 18, Column 15, Line 33, before "the", insert --with--.

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*